United States Patent [19]

Anderson et al.

[11] Patent Number: 5,196,470

[45] Date of Patent: Mar. 23, 1993

[54] WATER SOLUBLE ALCOHOL BASED NONWOVEN BINDER FOR WATER SWELLABLE, SOLUBLE OR SENSITIVE FIBERS

[75] Inventors: Stewart C. Anderson, Eden Prairie; Richard Malmsten, Vadnais Heights, both of Minn.

[73] Assignee: H. B. Fuller Licensing & Financing Inc., Wilmington, Del.

[21] Appl. No.: 663,407

[22] Filed: Mar. 1, 1991

[51] Int. Cl.$^5$ .................... C08F 220/06; C08K 5/05
[52] U.S. Cl. .................... 524/379; 524/388; 524/389; 528/489
[58] Field of Search ........... 524/379, 388, 389; 528/489

[56] References Cited

U.S. PATENT DOCUMENTS

| | | | |
|---|---|---|---|
| 2,897,172 | 7/1959 | Maeder | 524/389 |
| 3,927,199 | 12/1975 | Michelli et al. | 524/379 |
| 4,230,613 | 10/1980 | Wolinski et al. | 526/303 |
| 4,609,431 | 9/1986 | Grose et al. | 162/135 |
| 4,892,533 | 1/1990 | Le-Khac | 524/916 |

FOREIGN PATENT DOCUMENTS

| | | | |
|---|---|---|---|
| 0056842 | 8/1982 | European Pat. Off. | 524/379 |
| 0312008 | 4/1989 | European Pat. Off. | |
| 1452325 | 10/1976 | United Kingdom. | |

Primary Examiner—Paul R. Michl
Assistant Examiner—Andrew E. C. Merriam
Attorney, Agent, or Firm—Merchant, Gould, Smith, Edell, Welter & Schmidt

[57] ABSTRACT

An alcohol based, water soluble binder composition for nonwoven material made from water swellable, water soluble or water sensitive fibers and related substances is provided comprising a substantially anhydrous solution of an acrylic polymeric resin, and an alcohol diluent. The water soluble binder composition effectively binds water swellable, water soluble or water sensitive fibers into a nonwoven material such as a fabric; the nonwoven material comprising a nonwoven web of a water swellable, soluble or sensitive fiber component.

4 Claims, 2 Drawing Sheets

WATER SOLUBLE ALCOHOL BASED NONWOVEN BINDER FOR WATER SWELLABLE, SOLUBLE OR SENSITIVE FIBERS

FIELD OF THE INVENTION

The invention relates to adhesive binders useful in binding fibrous materials into nonwoven structures. More particularly, the invention relates to an alcohol based water soluble binder composition for water swellable, soluble or sensitive fibers.

BACKGROUND OF THE INVENTION

Nonwoven fabrics are generally prepared by randomly assembling individual fibers to form a web and bonding the fibers by chemical, thermal, or mechanical means. Generally, the fibers are bonded by impregnating the web with a binder for the nonwoven material and heating the web at an effective temperature to volatilize the carrier and induce fiber/binder adhesion. These nonwoven fibrous materials are known to possess distinct advantages over conventional woven materials. Some of these advantages include absence of raveling, smoother surfaces, increased softness, improved hand, greater absorbency, improved loft, etc.

The binders used to impregnate nonwoven webs are typically aqueous polymeric dispersions or aqueous polymeric latices which form tough, coherent films upon drying. A wide variety of polymers are known to be used as latex binders. Latices including polymers made from the following monomers or monomer blends of vinyl acetate, styrene/butadiene, vinyl acetate/acrylate monomers, vinyl acetate/ethylene, acrylic acid esters, and the like are generally known. Any of the above polymers can be copolymerized with many different vinyl monomers having functional groups such as amide, methylol, glycidyl, carboxyl, isocyanate, etc.

Caimi et al., U.S. Pat. No. 4,176,108 discloses a latex binder for nonwoven webs comprising an acrylate and/or vinyl acetate based copolymer containing 2-hydroxyethyl or 2-hydroxypropyl acrylate or methacrylate, which is combined with an anionic and nonionic surfactant.

Acrylic based polymers and copolymers used in adhesive formulations are well known. Wolinski et al., U.S. Pat. No. 4,230,613 discloses a lacquer composition for coating a substrate, comprising acrylic polymers such as methyl methacrylate/butyl acrylate/acrylic acid terpolymers, a volatile solvent such as a mixture of toluene and isopropanol, and a tertiary amine activator.

When nonwoven fabric materials are made from water swellable, soluble or sensitive fibers, there are inherent problems, i.e., shrinkage and dissolution of the fibers, associated with the saturation, spray or print bonding of an aqueous-based binder onto such fibers, preventing the formation of a structurally sound nonwoven web. Therefore, a non-aqueous adhesive binder is needed for use in making nonwoven water swellable, soluble or sensitive fiber-based materials, so that the adhesive effectively binds such fibers to form a structurally sound nonwoven web.

SUMMARY OF THE INVENTION

The invention relates to an alcohol-based, nonwoven water soluble binder for water swellable, water soluble or water sensitive fibers which comprises a substantially anhydrous liquid composition containing an effective amount of an alkali metal salt of an acrylic polymeric resin and an effective amount of an alcohol diluent. The polymeric binder resin has a glass transition temperature of about $-18°$ to $+80°$ C. and effectively binds water swellable, soluble or sensitive fibers into a nonwoven material such as a fabric or batt. The invention also relates to various nonwoven water swellable, soluble or sensitive fiber-based materials comprising nonwoven webs of such fibers that are bound with the acrylic polymeric resin of the invention.

The resin is a synthetic polymer which may be synthesized from an acrylic acid ester, methacrylic acid ester, or both, in combination with a polymerizable alpha, beta ethylenically unsaturated carboxylic acid. The polymer is neutralized with a non-volatile, alcohol soluble, alkali-source and is dissolved in an alcoholic diluent. The alcoholic polymer solution is made free of a concentration of water that would be harmful to water swellable, soluble or sensitive fibers, and has no effect on the fibers of the nonwoven fabric or batt. However, when the nonwoven material made of the polymeric binder and nonwoven water swellable, soluble or sensitive fibers is brought into contact with an aqueous liquid, the water swellable fibers absorb the liquid and the water soluble fibers dissolve. The solubility of the binder can be controlled via judicious selection of the type and concentration of the unsaturated acid monomer and the alkaline material utilized to generate the carboxylate salt.

One aspect of the invention is the alcohol-based water soluble binder composition for water swellable, soluble or sensitive fibers. A further aspect of the invention is a water swellable, soluble or sensitive nonwoven fiber-based material such as a fabric or batt, in which the fibers are structurally fixed in the fabric or batt using the binder composition. Another aspect of the invention relates to various articles comprising water swellable, soluble or sensitive nonwoven materials. The invention further relates to the use of a nonwoven material made with the binder in attaching a design or an applique to a fabric substrate.

DETAILED DESCRIPTION OF THE INVENTION

Figure 1:
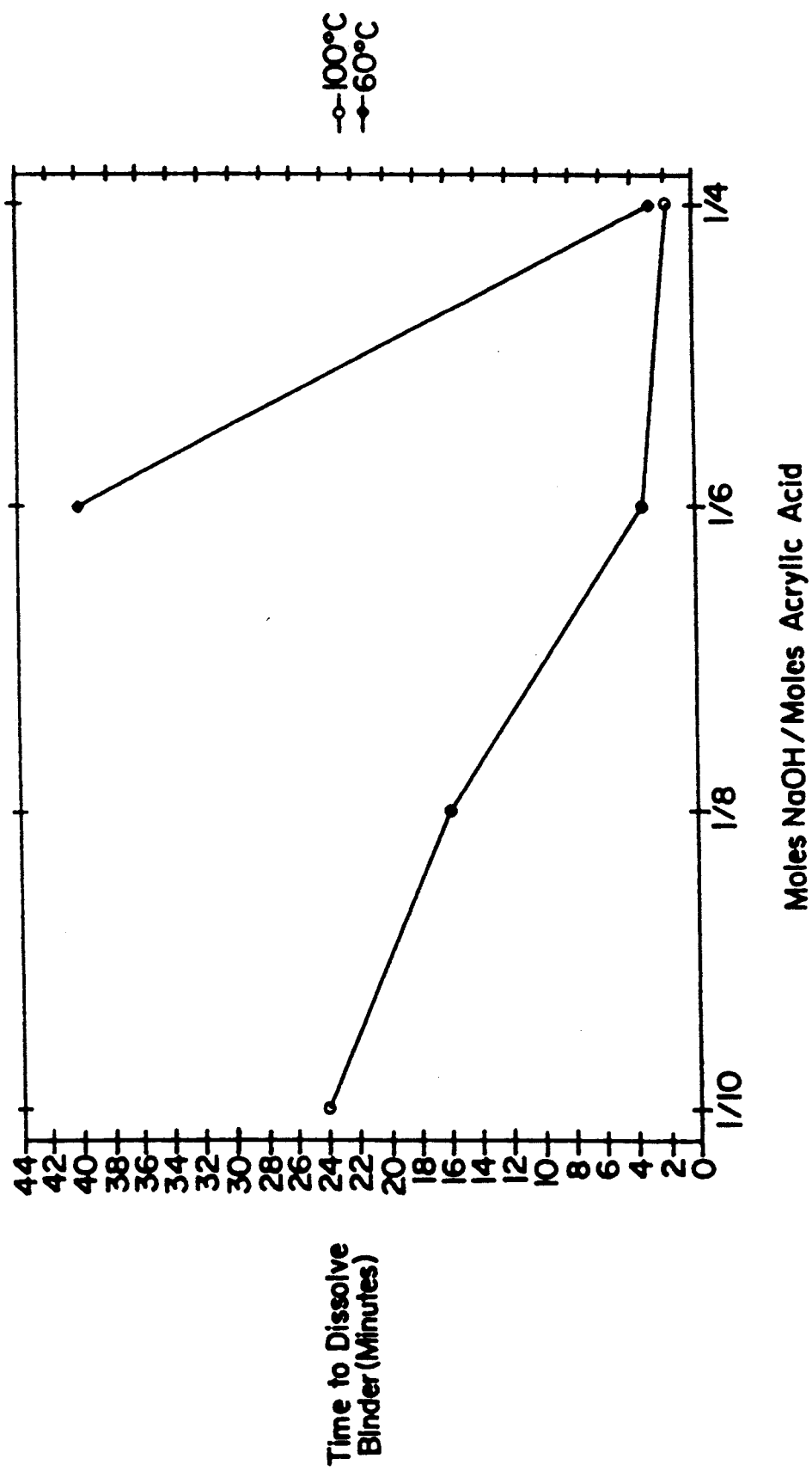
FIG. 1 is a graph depicting the time of solubilization of the acrylic polymer binder composition as a function of sodium hydroxide addition.

The invention resides in an alcohol-based binder composition used to form a nonwoven material from water swellable, soluble or sensitive fibers. The binder composition comprises a substantially anhydrous solution containing an effective amount of an alkali metal salt of an acrylic polymeric binder and an effective amount of an alcohol diluent. The polymer can effectively bind the water swellable, soluble or sensitive fibers into a nonwoven material.

ACRYLIC POLYMERS

The acrylic polymer composition can be formed from a variety of thermoplastic acrylic polymers. Suitable monomers useful in preparing the polymeric resin include esters of acrylic acid or methacrylic acid, and alpha, beta ethylenically unsaturated carboxylic acids. These monomers can be represented by the following general formula:

wherein R is hydrogen or methyl, and $R_1$ is hydrogen (in the instance an acid is used) or an alkyl chain of length from 1 to 16 carbon atoms. The binder resin is a synthetic vinyl polymer which may be synthesized preferably from any one of the acrylic acid or methacrylic acid esters in combination with an alpha, beta ethylenically unsaturated carboxylic acid.

Representative monomers which can be employed include acrylic acid, methacrylic acid, methyl acrylate, ethyl acrylate, propyl acrylate, n-butyl acrylate, pentyl acrylate, hexyl acrylate, 2-ethylhexyl acrylate, heptyl acrylate, octyl acrylate, nonyl acrylate, decyl acrylate, dodecyl acrylate, tetradecyl acrylate, hexadecyl acrylate, isopropyl acrylate, isobutyl acrylate, sec-butyl acrylate, 2-methylbutyl acrylate, 3-methylbutyl acrylate, 1-ethylpropyl acrylate, 2-methylpentyl acrylate, 2-ethylbutyl acrylate, 1,3-dimethylbutyl acrylate, 1-methylhexyl acrylate, 2-ethylhexyl acrylate, 1-methylheptyl acrylate, 4-ethyl-1-methyloctyl acrylate, 4-ethyl-1,1-isobutyloctyl acrylate, allyl acrylate, 2-methylallyl acrylate, 1-methylallyl acrylate, 2-butenyl acrylate, 1,3-dimethyl-3-dibutenyl acrylate, 3,7-dimethyl-7-octenyl acrylate, 3,7-dimethyl-2,6-octadienyl acrylate, 3,7-dimethyl-6-octenyl acrylate, tert-butyl acrylate. Representative ester monomers of methacrylic acid which can be used include methyl methacrylate, ethyl methacrylate, n-propyl methacrylate, isopropyl methacrylate, n-butyl methacrylate, isobutyl methacrylate, sec-butyl methacrylate, tert-butyl methacrylate, n-hexyl methacrylate, n-octyl methacrylate, isooctyl methacrylate, decyl methacrylate, n-dodecyl methacrylate, n-tetradecyl methacrylate, n-hexadecyl methacrylate, 2-ethylhexyl methacrylate, allyl methacrylate, oleyl methacrylate, 2-propynyl methacrylate, and the like. The above monomers may be employed separately or in various mixtures in forming the polymeric binder resin.

The polymeric resin preferably comprises an alpha, beta ethylenically unsaturated carboxylic acid, along with a $C_{1-6}$ alkyl acrylate, a $C_{1-6}$ alkyl methacrylate, or both. A particularly preferred polymeric resin comprises methyl methacrylate, n-butyl acrylate, and acrylic acid or methacrylic acid or mixtures thereof.

The polymeric resin has a glass transition temperature of about $-80°$ to $+80°$ C., preferably about $-18°$ to $+80°$ C. The glass transition temperature (Tg) is defined as the temperature above which the polymer has acquired sufficient thermal energy for rotational motion and torsional oscillation to occur about the majority of the bonds.

The acrylic polymeric resin is employed in a formulation in which at least some of the polymerized vinyl carboxylic acid is in an alkali metal salt form so that the binder is water soluble. The carboxylic acid bearing acrylic polymer is neutralized with an amount up to a stoichiometric amount of a non-volatile, alcohol soluble alkali. The solubility of the binder can be adjusted via the type and concentration of the primary alkali utilized to generate the carboxylate salt. A variety of alcohol soluble alkalis may be utilized in forming the alkali metal salt of the polymeric resin. These include sodium hydroxide, potassium hydroxide, etc.

The polymeric resin can comprise about 0 to 90 wt-% of a $C_{1-6}$ alkyl acrylate, about 0 to 90 wt-% of a $C_{1-6}$ alkyl methacrylate, and about 0.5 to 30 wt-% of an alpha, beta ethylenically unsaturated carboxylic acid, based on the binder composition. The polymeric resin preferably comprises about 5 to 85 wt-% of a $C_{1-6}$ alkyl acrylate, about 5 to 85 wt-% of a $C_{1-6}$ alkyl methacrylate, and about 1 to 25 wt-% of an alpha, beta ethylenically unsaturated carboxylic acid, based on the binder composition. Most preferably, the polymeric resin comprises about 10 to 65 wt-% of a $C_{1-6}$ alkyl acrylate monomer, about 10 to 70 wt-% of a $C_{1-6}$ alkyl methacrylate monomer, and about 15 to 25 wt-% of an alpha, beta ethylenically unsaturated carboxylic acid monomer.

ALCOHOL DILUENT

The water soluble binder composition of the invention also comprises an effective amount of a substantially anhydrous alcohol diluent. The alcohol diluent can be selected from a variety of well known and available alcohols or alcohol containing solvents such as methanol, ethanol, isopropanol, n-propanol, n-butanol, etc. Preferred alcohols for use in the binder composition are methanol, isopropanol, or mixtures thereof.

The polymeric resin is preferably polymerized in isopropanol to the desired molecular weight and level of polymerization (i.e., MW=5000 to 20,000; 98+%). This system is then let down with methanol to reduce the viscosity to aid in pumping and handling of the binder composition. The alcohol diluent comprises about 20 to 80 wt-%, preferably about 30 to 50 wt-% of the binder composition.

A particularly preferred polymeric nonwoven binder composition for water swellable, soluble or sensitive fibers comprises a substantially anhydrous liquid composition containing about 80 to 20 wt-%, preferably 50 to 30 wt-% of an alcoholic diluent and about 20 to 80 wt-%, preferably 50 to 70 wt-% of a neutralization product of a water soluble polymeric resin and an alkali metal hydroxide, based on the binder composition. The resin most preferably comprises about 10 to 65 wt-% of a $C_{1-6}$ alkyl acrylate monomer, about 10 to 70 wt-% of a $C_{1-6}$ alkyl methacrylate monomer, and about 15 to 25 wt-% of an alpha, beta ethylenically unsaturated carboxylic acid monomer. The alkyl acrylate monomer preferably comprises n-butyl acrylate, the alkyl methacrylate monomer preferably comprises methyl methacrylate, and the carboxylic acid monomer preferably comprises acrylic acid or methacrylic acid or mixtures of both. The polymeric resin preferably has a glass transition temperature of from about $-18°$ to $80°$ C. and effectively binds water swellable, soluble or sensitive fibers into a nonwoven material such as a fabric or paper product.

The polymeric binder of the invention can be made by the following procedure. An alcohol diluent such as isopropanol and a free radical catalyst such as Vazo 64 (Azobisisobutyronitrile) are charged into a mixing vessel with sufficient agitation to disperse the catalyst and a nitrogen purge is started. The selected monomers are blended together and an initial charge of about 5–15 mass-% of the monomer blend is charged into the mixing vessel. The mixture is then heated. The mixture is held at a temperature of about 70°–80° C. During this holding period the viscosity increases as the polymerization is initiated and the polymer chains propagate. After an initial hold period of approximately 30 minutes, the remaining amount of the monomer blend is fed continuously or incrementally into the initial polymeric liquor which is maintained at about 70°-80° C. An alcohol diluent such as methanol is added as needed for uniform mixing, with approximately 15% of the alcohol added at the first hour mark and another 50% added over the course of the monomer feed if necessary. When methanol is added, the batch temperature will quickly decline and it may not be possible to keep the temperature at 72° C. due to methanol reflux. The process should be continued at as high a temperature as possible without heavy reflux (though still less than 78° C.). The polymer solution is then held for 2 hours to allow for complete conversion of monomer to polymer. After the hold period, any leftover alcohol is added to the solution which is then cooled below 30° C. Sodium hydroxide is predissolved in an alcohol diluent such as methanol and agitated to dissolve the sodium hydroxide. The sodium hydroxide/methanol solution is then slowly added to the polymer solution and mixed for about 15 minutes. The solids content of the resulting polymeric binder composition can then be adjusted by evaporation or addition of an alcohol such as methanol.

The polymeric binder of the invention can also be made by standard emulsion polymerization techniques using surfactants or emulsifying agents in the continuous phase to stabilize the monomers dispersed in the dispersed phase. The surfactants or emulsifying agents can be low molecular weight surfactants or polymerizable surfactants such as copolymerizable monomers having surface active moieties. Emulsion polymerization can take place under normal pressure and at a temperature under 100° C., preferably from 20° C. to 80° C. Generally the monomers are mixed with water and the polymerization reaction is initiated with a water soluble free radical catalyst. The aqueous system provides a medium for the dissipation of heat from the propagating exothermic addition polymerization process. The two phase system of water and the monomers employs a surfactant or emulsifying agent to reduce the interfacial tension and disperse the monomers in the constant or aqueous phase.

The many parameters of the emulsion polymerization technique can be adjusted by those skilled in the art to obtain particular desired results The comonomers can be added to the aqueous phase gradually or in one charge. Initiators can also be added according to a variety of possible schedules. Thus, one or more of the comonomers can be emulsified first in the stirred aqueous phase before initiation has begun, or a pre-emulsion of monomer can be maintained in the presence of surfactant and initiator. The monomers can be added continuously or in increments. Similarly, depending upon the reactivity of the other monomers involved, the polymerizable surfactant may be introduced into the emulsion polymer at the time of polymer initiation, or it may be periodically introduced throughout polymerization, or continuously introduced during the course of the polymerization. During the polymerization reaction, the system is agitated continuously at temperatures essentially below 100° C. until the polymerization has essentially approached 100% conversion.

Surfactants which can be employed in the emulsion polymerization reaction to enhance emulsion stability can include any of the known surfactants such as monophenol ethoxylates, sodium dodecyl benzene sulfonate, sodium dioctyl sulfosuccinate, octylphenol ethoxylates, octylphenol ethoxylate sulfonates, etc. Polymerizable monomers which can be employed as surfactants include sulfonic acid or sulfonate-containing acrylic monomers. Examples of these monomers include a sulfonic-acid substituted ethyl acrylate, sodium sulfonate-substituted n-butyl methacrylate, sodium sulfonate-substituted ethyl methacrylate, etc. The sulfonic acid or sulfonate end group in the above monomers provides emulsion stability without significantly affecting water sensitivity of the dried polymer. A preferred monomer of this type is a 2-sulfoethyl methacrylate known as Sipomer 2-SEM available from Grace Chemical. The amount of surfactant employed in producing the polymeric binder of the invention is within the range of about 0.1 to 1 wt-%, preferably about 0.2 to 0.5 wt-%, based upon total weight of the polymer.

Chain transfer agents can be employed to modify the molecular weight of the polymeric composition. A useful transfer agent is lauryl mercaptan, e.g., n-dodecyl or t-dodecyl mercaptan. The chain transfer agent is generally included in the compositions at a relatively low level, preferably within a range of about 0.01 to 2 wt-% based on the total weight of the polymer.

A polymerization initiator that is dissociated via heat is used to advantage in certain preferred emulsions of the invention as a source of free radical species. The initiator is typically present in an amount of about 0.01 to 4 wt-%, based on the total weight of the emulsion. Sodium persulfate, potassium persulfate, ammonium persulfate, hydrogen peroxide, and t-butyl hydroperoxide are all useful initiators.

The polymeric binder composition of the invention may also contain other additives well known to those skilled in the art including pH control agents, foam control agents, dyes, crosslinking components, etc.

Once the emulsion polymerization is complete, water can be removed by spray drying (evaporation) to form a dry, finely divided high molecular weight polymeric particulate. An alcohol diluent and an alkali source such as a methanol/sodium hydroxide solution is added to the dry polymer to form the binder composition of the invention.

NONWOVEN FIBER MATERIALS

There are many nonwoven fiber structures and materials which have been produced from a variety of fiber types. A nonwoven fabric is an assemblage of staple fibers and/or yarns more or less randomly formed into a configuration of a mat or web and given dimensional stabilization by one of three methods. These methods include mechanical entanglement (needlepunching), thermal bonding (spunbonding), and chemical (adhesive) bonding. Nonwoven fabrics can be employed in many different end uses wherein textile-like properties, such as softness, drapability, strength and abrasion resistance are desired. The term "fabric" as used in this disclosure refers to fabrics made from nonwoven fibers and/or webs and may also include polymeric netting, meshes and screens fabricated as one web.

In conventional textile fabrics, the basic elements are yarns or in special cases monofilaments. Yarns are composed of fibers that have been parallelized and twisted by a process called spinning to form strong cohesive elements. In making woven textile fabrics, the yarns (or the monofilaments) are interlaced, looped or knotted together in a highly regular repetitive design in any of many well known ways to form a fabric. The fabric strength and other physical properties are derived from the friction of individual fibers within each yarn and the friction between adjacent yarns. In nonwoven fabrics, the basic elements are individual fibers and/or fibrous yarns, and tensile properties of these fabrics are derived from chemical/adhesive bonding, or frictional forces between individual fibers. Nonwoven textile fabrics are porous, textile-like materials manufactured by processes other than spinning, weaving, knitting or knotting. Nonwoven fabrics are less costly than woven or knitted material, yet are more or less comparable in physical properties, appearance, and weight.

A few basic elements can be varied and controlled to produce a broad range of nonwoven fabrics. These include fiber types and physical variations, the web and the average geometric arrangement of its fibers as predetermined by its method of forming and subsequent processing, the bonding of the fibers in the web and their subsequent reinforcement. Each of the above elements can be varied and can thus exert a powerful influence, alone and in combination, on the final fabric properties.

A fibrous web is the common constituent of all nonwoven fabrics. The characteristic properties of the base web are determined by fiber geometry, largely as determined by mode of web formation; fiber characteristics, both chemical and mechanical; web weight; and further processing including calendering, fiber rearrangement, and fiber entanglement. Among the important aspects of fiber geometry are the average direction of fiber orientation, either isotropic or anisotropic; the longitudinal shape of the fibers, whether predominantly elongated or curled; interfiber entanglement; surface morphology, and residual crimp. The conventional base starting material for the majority of nonwoven fabrics is a fibrous web comprising any of the common textile-like fibers, or mixtures thereof, the fibers varying in average length from about 0.3 centimeter to about 6.3 centimeters. Exemplary of such fibers are the natural fibers such as cotton and wool and the synthetic or man-made fibers of rayon, polyester, polyethylene, polypropylene, teflon, nylon, acrylic fibers, and polyvinyl alcohol among others.

Nonwoven fabrics can be made from staple length fibers, endless filaments, and very short fibers (primarily wood pulp). As applied to regenerated cellulose and synthetic fibers, staple fibers are of relatively uniform length, e.g. 1.3-10.2 centimeters, and can be processed on conventional textile machinery. Since regenerated cellulose and other extruded fibers are endless as formed, they are cut during the manufacturing process to a specific length to meet a processing or market need. Extruded fibers also are produced as continuous filaments. Nonwoven fabrics that are made from staple fibers have a soft hand and tend to have more loft than fabrics that are made from endless filaments. Staple and endless filament fiber webs lead to products that differ substantially in their properties.

Nonwoven fibrous structures frequently consist of a more or less random yet homogeneous agglomeration of long and short fibers. Long fibers can be fibers of both natural and synthetic origin and are suitable for textiles. Short fibers are suitable for paper making and are generally less than about 0.6 centimeter long, such as wood pulp fibers or cotton linters. It is known to those skilled in the art that strong nonwoven structures can be made by randomly blending short fibers with strong long fibers. Random distribution of the blended fibers results in an isotropic web; i.e., a structure that has uniform strength in the machine and cross machine direction. The fibers can also be directionally disposed or aligned, resulting in a fabric that is strong in the direction of alignment.

The desired utility and characteristics of the nonwoven end product dictate the types of fibers and relative proportions of long and short fibers in a web. The desired characteristics may include, for example, tear resistance, abrasion resistance, extensibility, tensile strength, absorption or nonabsorption of different liquids, heat sealability, resistance to delamination, water solubility or water sensitivity. The fibers, as defined by their chemical composition and as a result of their physical-mechanical properties, determine the ultimate fabric properties. Other determinants, such as web structure and bonding, maximize inherent fiber characteristics, e.g. strength, resilience, abrasion resistance, chemical resistant properties, absorbency or repellency. In addition to the substantial numbers and variety of natural, regenerated, and synthetic fibers that are readily available, mechanical differences are intentionally introduced in fibers that ultimately alter web and finished product properties. The variations that may be produced include fiber length, diameter, crimp, cross-sectional shape, and fiber finish.

There are many different web forming techniques but the two major processes are dry forming, including carding/garnetting and air laying, and wet forming. In the dry forming process of carding/garnetting, individual natural and/or synthetic fibers are metered and uniformly distributed by mechanical means to form a web. Fiber-to-fiber bonding is then achieved by the addition of chemical binders or by heat fusion. Following drying of the bonding chemicals, the resulting web is wound into a roll, which is ready for post treatment or conversion into a finished product. Conventional carding/garnetting methods used to produce nonwoven webs are generally limited to textile-like fibers. The carding/garnetting process is particularly useful in making nonwoven diaper top sheets, interlinings, wipes, and sanitary napkin cover sheets. The webs produced are typically anisotropic.

Like carding/garnetting, the air laying process meters individual natural and/or synthetic fibers into an unbonded web. However, distribution is accomplished by continuously suspending the fibers in an airstream and then conveying them onto a screen to form a web. By controlling the characteristics of the airstream, fiber orientation can be more isotropic than in carding/garnetting. The fibers in the web are then mechanically, chemically or thermally bonded and wound into a finished roll. The air laid process is particularly useful for making nonwoven toweling. Dry formed fabric weights usually range from about 0.3 to 6 oz. per square yard and exhibit a range in caliper from about 3 to 15 mils.

In the wet forming nonwoven process, individual natural and/or synthetic fibers are suspended in water to form a uniform dispersion. As the fiber and water suspension flows onto a forming wire screen, the water passes through, resulting in a uniform fibrous web. Additional water is then squeezed out of the web and remaining water is removed by drying. Chemical and/or thermal bonding is typically used to impart structural integrity to the wet formed web. Following bonding, the fabric is wound up into a finished roll ready for subsequent operations. Typical end use applications for nonwoven fabrics formed by wet laying processes include toweling/wipes, filtration, shoe components, and surgical gowns. The suspension of fibers in water results in a random orientation of the fibers. The wet laying process also permits various chemicals and binders to be added to the fibers as they are formed into a web. Since the manufacturer can add chemicals before and after web formation, the process is highly flexible. Fabric weights usually range from about 0.3 to 16 oz. per square yard, and calipers generally range from about 2.3 to 190 mils.

A needlepunched fabric is produced by introducing a fibrous web, already formed by carding./garnetting or air laying, into a machine equipped with groups of specially designed needles. While the web is trapped between a bed plate and a stripper plate, the needles pierce it and reorient the fibers so that mechanical entanglement is achieved among the individual fibers. Often, the web of fibers is carried into the needlepunching section of the machine on a lightweight nonwoven support substrate. This is done to improve the finished fabric strength and integrity. The needlepunching process is generally used to produce fabrics which have high density yet retain some bulk. Fabric weights usually range from about 1.7 to 10 oz. per square yard and calipers generally range from about 15 to 160 mils. Typical end uses of nonwoven needlepunched fabrics include blankets, filter media, coated fabric backings, carpeting and carpet backings, landau top substrates, geotextiles, auto trunk liners, etc.

Web bonding is commonly achieved by use of chemical or adhesive binders. Methods for the application of adhesive binders include print bonding, saturation bonding, spray bonding, and foam bonding. In print bonding, gravure or etched areas are selected in a specific pattern for applying the adhesive which determines the strength, softness and drape values of the nonwoven fabric. In foam bonding, which is energy efficient, the latex binder is diluted with air rather than water allowing for decrease heat demand during drying. Bonding can also be effected by interfiber friction from mechanical entanglement (such as by needlepunching), and by thermal fusion, by such methods known as spunbonding, where molten filaments of thermoplastic polymer are allowed to contact each other and bond. Fibrous webs can be further reinforced by woven fabrics, plastic nettings, cross-laid yarns, scrims, foams, and polymer films. For an extensive treatise on nonwoven textile fabrics, see *Nonwoven Bonded Fabrics*, Vol. 1, (Ellis Horwood Ltd) 1985.

When nonwoven fabric materials are made from water swellable, soluble or sensitive fibers and the like, there are inherent problems associated with the saturation, spray or print bonding of an aqueous-based binder onto such fibers, preventing the formation of a structurally sound nonwoven web. The alcohol based water soluble polymeric binder of the invention can be used to form a water swellable, soluble or sensitive nonwoven material comprised of water swellable, soluble or sensitive fibers, and an effective binding amount of a water soluble acrylic polymeric resin for binding the nonwoven web. The binder composition of the invention bonds the fibers into a nonwoven material when the binder impregnates the nonwoven fibrous web.

Any fiber, yarn, particulate or other configuration which has the required specifications to be formed into a nonwoven fibrous web or polymeric film and is water swellable, soluble or sensitive may be used. The material formed from the fibers and binder is preferably a fabric or paper product that readily absorbs an aqueous liquid when the fiber component used is water swellable. The fabric dissolves or dissipates when contacted with an aqueous liquid when the fiber component is water soluble or sensitive. Preferred water swellable fibers and particulates are made from super absorbent polymers such as the polyacrylates and their acrylic acid salts. Preferred water soluble fibers are derived from polyvinyl alcohol and preferred water sensitive fibers include rayon and unaltered cellulosic fibers. These fibers can be employed separately or in various blends when forming the nonwoven material.

Polyvinyl alcohol fibers are obtainable by dry or wet extruding or spinning from their aqueous solutions and by definition, are composed of at least about 50% by weight of vinyl alcohol units $(CH_2—CHOH)_n$ in which the total number of vinyl alcohol units in any one or more of the various acetyl units is at least about 85% by weight of the fiber. Since the vinyl alcohol molecule as such is nonexistent as a monomer, polyvinyl alcohol is usually prepared by polymerization of vinyl acetate into polyvinyl acetate, followed by conversion by alcoholysis, hydrolysis, saponification, or the like to polyvinyl alcohol.

The nonwoven web of the invention may be formed by using any of the known aforementioned conventional web forming techniques. The particular method used in forming the nonwoven web is dependent on the particular fiber or fiber blend employed, the thickness of the web, whether the fibers are to be oriented or deposited at random, etc. The acrylic polymeric binder composition may be applied to the nonwoven fiber web in any suitable manner such as by spraying, printing, roll coating, padding, or the like. The amount of the binder composition should be from about 30 to 60% by weight at the time of application to the web, although higher or lower amounts may be used as necessary. The binder composition may be applied to one or both surfaces of the web or may be distributed through the infrastructure of the web as well.

The drying of the web is normally conducted by passing the fibrous material through one or more ovens or heating chambers maintained at temperatures of between about 80° C. to 180° C., preferably about 110° C. to 150° C. The conditions of drying are controlled so that no appreciable deterioration or degradation of the fibers or polymeric resin occurs. The time required for drying will depend on the thickness of the web, the line speed, the amount of binder used, the solids content in the binder, etc. Generally, drying is carried out until the ultimate physical characteristics of the finished nonwoven fibrous material are developed.

The nonwoven web comprises about 30 to 95 wt-% fiber, preferably about 50 to 95 wt-% fiber, based on the unbonded nonwoven material. The polymeric binder resin comprises about 5 to 70 wt-%, preferably about 5 to 50 wt-%, based on the unbonded nonwoven material.

The finished article, obtained by impregnation of the binder composition into a nonwoven web, is a chemically bonded nonwoven fiber-based material which is water swellable, soluble or sensitive. The resulting material may be used in any application wherein nonwoven water swellable, soluble or sensitive materials are employed. Various paper products can be made from water swellable, soluble or sensitive fibers employing the binder of the invention such as paper towels, flushable bathroom tissue and other paper products having desired water soluble or sensitive characteristics. Various water swellable, soluble or sensitive fabrics can also be made from a nonwoven web and the binder composition.

The polymeric binder composition of the invention may be used in forming an article comprising a water soluble or sensitive nonwoven fabric and an applique supported by the nonwoven fabric. The nonwoven fabric comprises a nonwoven web of a water soluble or water sensitive fiber component and an effective binding amount of a water soluble acrylic polymeric resin for binding the nonwoven web. The nonwoven fabric readily dissolves when contacted with an aqueous liquid. The applique is preferably made of a woven material and is attached to or supported by the nonwoven fabric using any suitable mechanical means.

The nonwoven fabric material having the applique attached thereon can be used in a method of attaching the applique to a fabric substrate such as a garment. The method comprises the step of applying an article, comprising an applique and a water soluble or sensitive nonwoven fabric, to the fabric substrate mechanically or chemically. The nonwoven fabric comprises about 50 to 95 wt-% of a water soluble or water sensitive fiber component and about 5 to 50 wt-% of a water soluble acrylic polymeric resin for binding the nonwoven web. The polymeric binder has a glass transition temperature of about $-18°$ to $+80°$ C. The fabric substrate having both the water soluble nonwoven fabric and the applique attached thereon (either mechanically or chemically) is contacted with an aqueous liquid, thereby dissolving the nonwoven fabric from the fabric substrate with the applique remaining attached to the fabric substrate. This method allows for a variety of appliques to be attached to various fabrics or garments, imparting a decorative component to the fabric or garment.

Since the water soluble polymeric binder for forming the fiber based nonwoven materials is a thermoplastic, the nonwoven materials impregnated with the binder can be dry bonded or heat sealed to a variety of substrates without using additional adhesive. These laminations can then be used in generating a variety of nonwoven composites.

The polymeric binder of the invention may also be employed as a sizing composition for water swellable, soluble or sensitive fibers, and can be applied to separate fibers or fibrous yarns or bundles to enhance the strength of such materials and impart novel dissolution properties. A sized fiber comprises a water swellable, water soluble or water sensitive fiber component, and a sizing composition on said fiber of a water soluble acrylic polymeric resin, wherein the resin has a glass transition temperature of about $-18°$ to $+80°$ C. A sized fibrous yarn comprises a fibrous yarn component comprising water swellable, soluble or sensitive fibers, and the above sizing composition on the yarn for binding the fibers. The fiber component of the sized fiber or yarn can comprise any of a number of materials such as polyvinyl alcohol, rayon, cellulose, polyacrylic acid salts, etc. The sized yarn can be made from a single fiber type or from blends of various fiber types.

The binder composition of the invention may also be used in forming a nonwoven mesh reinforcement article for poured cement or concrete. The reinforcement article comprises a nonwoven mesh comprising a nonwoven web of a water swellable, soluble or sensitive fiber component and an effective binding amount of the water soluble anionic acrylic polymeric resin on the nonwoven web for binding the nonwoven web. The article provides effective reinforcement and strengthening properties to poured cement or concrete. A reinforced cement or concrete composition comprises a major portion of cement or concrete and the above nonwoven mesh reinforcement article incorporated in the cement or concrete composition.

The polymeric binder of the invention may be used to make nonwoven moisture absorbing wipes that effectively absorb a spilled aqueous liquid. The wipes can be made by fibrillation of water swellable fibers, which is the active process of forming fibers or fibrils into fiber pulp, which can in turn be bound into a nonwoven web by the polymeric binder composition of the invention in its alkali metal salt form. The polymeric binder of the invention used in making the nonwoven wipe material has the ability to control the absorbency of the wipe. The concentration of alkali metal salt in the binder can control the rate of swelling of the absorbing material. As the salt content is increased in the binder, the rate of absorbency of the wipe is increased. A super absorbing composition, such as polyacrylate, can be combined with the fiber pulp of water swellable fibers and bound by the polymeric binder composition of the invention in its salt form to produce a nonwoven super absorbing wipe material. This material can further be incorporated with a biocide such as quaternary ammonium compounds, related compounds with similar biocidal activity or other antimicrobial agents. This biocidal nonwoven absorbing wipe can be used to clean up and disinfect biological spill areas caused by spilled blood or other body fluids which can be hazardous.

The polymeric binder of the invention may also be used in formulating various nonwoven materials which can be employed in moisture absorbent articles such as disposable diapers, an incontinent pad, a bed pad, or a feminine pad. Broadly, the absorbent articles are made by joining to a substrate, typically a plastic film substrate, an absorbent layer covered with a nonwoven overlaying fabric. More specifically, a moisture absorbent article comprises a polymeric film substrate, at least one absorbent layer, and an elastic banding material, wherein the absorbent layer and the elastic are independently bonded to the substrate and the absorbent layer includes a nonwoven fabric comprising a nonwoven fibrous web and an effective binding amount of a water soluble acrylic polymeric resin on the nonwoven web for binding the nonwoven web.

Plastic substrates useful in absorbent articles comprise films made from polyethylene, polypropylene, polyethylene terephthalate, polyvinyl chloride, polyvinylidine chloride and other materials capable of film formation. Elastic banding materials are typically adhesively attached to the plastic film substrate often under a film or tissue overlayer. Such elastomers are polymeric substances with molecular memory in that when such materials are placed under stress, they elongate, then when the stress is removed they return to their original dimensions. Elastomeric polymers are typically polymers of moderate molecular weight. Representative elastomeric polymers include styrene-butadiene copolymers, isobutyleneisoprene copolymers, polychloroprene systems (Neoprene ®, duPont), polyurethanes, polysulfide rubbers, polyacrylate elastomers comprising the copolymerization of ethyl acrylate and acrylic acid-lower alkanol esters, silicone elastomers, fluoro-elastomers, ethylene-propylene elastomers, and mixtures thereof. The absorbent or permeable layer can comprise absorbent tissue or fluff, covered by the nonwoven fabric. The tissue or fluff is typically a loosely formed cellulosic sheet of high porosity or permeability and is typically manufactured through the formation of finely divided cellulosic fibers. However, other materials can be used to form highly absorbent fluff or pulp layers. Nonwoven webs of the fabric can comprise natural or synthetic fibers or mixtures thereof and can be made through the aforementioned processes. Preferable synthetic materials which can be used in forming the nonwoven fabric layers include fibrillated wood pulp, polyacrylate, polyacrylic acid salts, rayon, polyester, polypropylene, polyethylene, nylon, etc. The nonwoven fabric preferably comprises a nonwoven web of a water swellable fiber component and an effective binding amount of the water soluble acrylic polymeric resin of the invention.

WORKING EXAMPLES

The following working Examples are illustrative of the invention and contain a best mode.

EXAMPLES 1 and 2

The acrylic polymeric binder compositions of Examples 1 and 2 were made by the following procedure. The ingredients of Examples 1 and 2 and respective amounts are listed in Table I below.

TABLE I

| Ingredients | Wt. of Ingredient (g.) | |
|---|---|---|
| | Example 1 | Example 2 |
| Isopropanol | 50.00 | 100.00 |
| Vazo 64 (Azobisisobutyronitrile) | 3.30 | 3.30 |
| Methyl Methacrylate | 158.60 | 158.60 |
| n-Butyl Acrylate | 296.90 | 296.90 |
| Acrylic Acid | 85.00 | 85.00 |
| Diallyl Maleate | 1.98 | 1.98 |
| n-Dodecyl Mercaptan | 5.71 | 5.71 |
| Methanol | 66.00 | 66.00 |
| Vazo 64 (Azobisisobutyronitrile) | 0.66 | 0.66 |
| Methanol | 200.00 | 200.00 |

A polymer solution was made by charging isopropanol and Vazo 64 (a catalyst) into a mixing vessel with sufficient agitation to disperse the Vazo 64, and a nitrogen purge was then started. The monomers of methyl methacrylate, n-butyl acrylate, and acrylic acid as well as the diallyl maleate were then blended together. Next, 7% of the monomeric blend (38.37 g.) was charged into the mixing vessel and the mixture was heated The nitrogen purge was stopped at 55° C. and at 68° C. the mixture was held for ½ hour, allowing the temperature to rise to 72° C. During this hold period the viscosity increased as the polymerization was initiated and followed by propagation. After the hold period the remaining amount of the monomer blend and the other ingredients (see Table I) were fed into the mixture and the solution was maintained at 74°-78° C. After the remaining Vazo 64 was added to the mixture, methanol was added as needed for uniform mixing. Approximately 15% of the methanol was added at the first hour mark and another 50% was added over the course of the monomer feed. When the methanol was added, the batch temperature quickly dropped. The solution was then held for 2 hours to allow residual monomers to polymerize. The last of the methanol was then added, and the vessel was cooled to room temperature.

Separate from the polymerization, a solution was made containing 16.32 g. of sodium hydroxide and 84 g. of methanol. Two 16.7 g. aliquots of this solution was then added to a 100 g. sample of Example 1 and a 105.7 g. sample of Example 2. Polymeric films of each of Examples 1 and 2 were then drawn down on a glass plate and allowed to dry overnight. The following day, the polymeric films were removed from the glass. A small quantity of film based on these polymer compositions were put into separate cups, and about 7 ml of water was added to the cups and the mixture was stirred. Both compositions of Examples 1 and 2 readily dissolved.

A 1:4 mix of the sodium hydroxide solution and the acrylic polymer composition of Example 1 was then made. A 10 ml. film was then prepared on release paper. The film was air dried and then placed in a 110° C. oven to complete the drying process. The film, when removed from the paper, had reasonable flexibility and tensile strength. The film was then placed in hot (near boiling) water and dissolved almost immediately.

EXAMPLES 3-10

Polymeric binder compositions were made in Examples 3-10 by a similar procedure as described above for Examples 1 and 2. The ratio of monomeric components in the terpolymer compositions of methyl methacrylate, n-butyl acrylate and acrylic acid are listed in Table II below. Also summarized in Table II is the glass transition temperature and sodium hydroxide/acrylic acid mole ratio for each Example.

TABLE II

| Example | Polymer Composition (MMA/BA/AA)* | Glass Transition Temperature (Tg °C.) | NaOH: Acrylic Acid Mole Ratio |
|---|---|---|---|
| 3 | 13.8/65.4/20.8 | −18 | 1:4 |
| 4 | 13.8/65.4/20.8 | −18 | 1:10 |
| 5 | 42.8/30.0/27.2 | +40 | 1:4 |
| 6 | 42.8/30.0/27.2 | +40 | 1:10 |
| 7 | 54.3/29.9/15.8 | +42 | 1:4 |
| 8 | 54.3/29.9/15.8 | +42 | 1:10 |
| 9 | 69.8/12.3/17.9 | +80 | 1:4 |
| 10 | 69.8/12.3/17.9 | +80 | 1:10 |

*MMA = methyl methacrylate
*BA = n-butyl acrylate
*AA = acrylic acid

As can be seen from Table II, two different sodium carboxylate levels were produced for each of four polymer compositions, including a sodium hydroxide:acrylic acid mole ratio of 1:4 and 1:10 for each of the polymer compositions. The polymer dissolution rate as a function of salt concentration was then determined at 60° C. and 100° C. The results of this determination are shown in the graph of FIG. 1. As can be seen from the graph, the polymer dissolution time decreased as the NaOH:acrylic acid mole ratio increased from 1:10 to 1:4 at the two indicated temperatures of 100° C. and 60° C.

EXAMPLE 11

A nonwoven polyvinyl alcohol (PVOH) mat and an acrylic binder, similar to Examples 1-10, was used to prepare a nonwoven fabric to determine tensile data. The characteristics of the PVOH mat are summarized in Table III.

TABLE III

| PVOH Mat | |
|---|---|
| Fiber type | PVOH, 99% hydrolyzed |
| Fiber length | 51 mm. |
| Fiber Denier | 3 |
| Nonwoven web type | Needlepunched PVOH fiber |
| Nonwoven web bases wt. | 3.5 oz/yd² |

The procedure used for polyvinyl alcohol web saturation was as follows. A 6"×10" sheet was cut from a needlepunched web. The acrylic solution polymer was then diluted with methanol, to approximately 10% solids. This diluted solution was then poured into an 8"×12" Pyrex pan. The polyvinyl alcohol fabric was then enveloped in a polypropylene scrim (Conwed TD-627). The scrim and fabric was then saturated in the dilute polymer solution for one minute to ensure complete penetration of the solution into the fabric. The saturated web/scrim was then placed between the rolls of an Atlas padder set at 20 psi. The scrim was then removed and the web was allowed to air dry. The desired number of specimens were then cut into 1"×8" specimens and used in T/E (tensile/elongation) studies using an Intelect 500.

Figure 2:
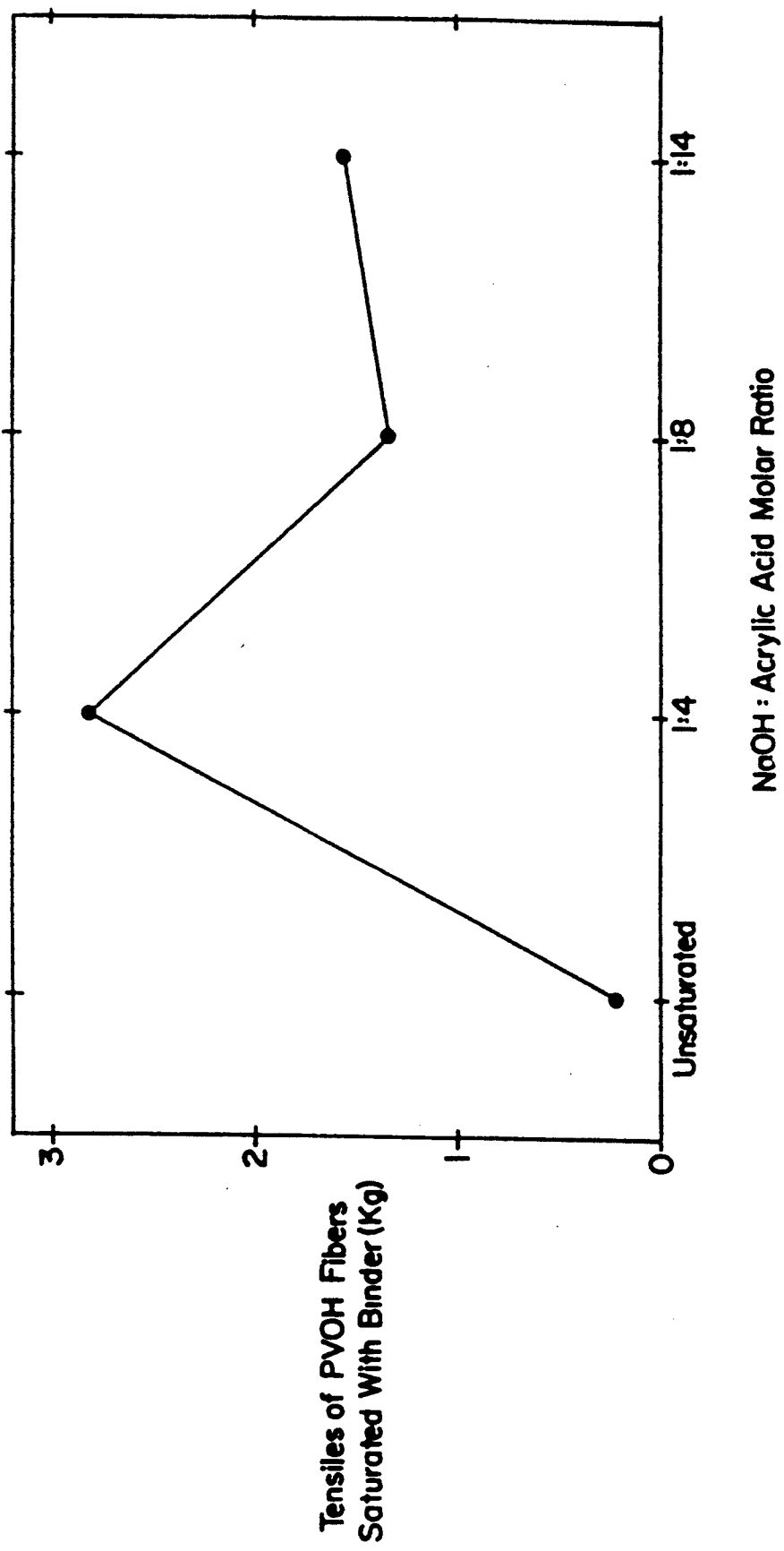
FIG. 2 is a graph depicting the tensile strength of a polyvinyl alcohol nonwoven fabric saturated with the acrylic binder composition as a function of sodium hydroxide addition.

Tensile data was developed on both an unsaturated and saturated PVOH mat. The polymer that was used to generate the saturated tensile data was a carboxyl functional acrylic terpolymer of methyl methacrylate/n-butyl acrylate/acrylic acid having a monomeric ratio of 70/12/18 and a glass transition temperature of 80° C. Sodium hydroxide was added to samples of the acrylic terpolymer in three different amounts to generate three different sodium carboxylate concentrations (i.e., 1:4, 1:8, 1:14 NaOH:acrylic acid mole ratio). The graph of FIG. 2 depicts the tensile data of an unsaturated PVOH mat and saturated PVOH mats with the three sodium carboxylate concentrations. As can be seen from the graph of FIG. 2, the saturated PVOH mat having the highest tensile strength had the highest sodium carboxylate concentration (1:4) in the binder.

The foregoing discussion and Examples are illustrative of the invention. However, since many embodiments of the invention can be made without departing from the spirit and scope of the invention, the invention resides wholly in the claims hereinafter appended.

We claim:

1. A nonwoven, water soluble binder composition useful for binding water swellable, water soluble or water sensitive fibers, in which said binder composition is a substantially anhydrous liquid comprising:
   (a) about 50 to 70 wt-% of a neutralization product of:
      (i) a water soluble polymeric resin comprising about 10 to 65 wt-% of a $C_{1-6}$ alkyl acrylate monomer, about 10 to 70 wt-% of a $C_{1-6}$ alkyl methacrylate monomer, and about 15 to 25 wt-% of an alpha, beta ethylenically unsaturated carboxylic acid monomer; and
      (ii) an alkali metal hydroxide; wherein said neutralization product has a mole ratio of alkali metal hydroxide to acid monomer of about 1:4 to 1:10 and has a controlled rate of solubilization resulting in a dissolution time of about 1 to 42 minutes which can be varied based on the concentration of acid monomer and alkali metal hydroxide utilized to generate the neutralization product; and
   (b) about 30 to 50 wt-% of an alcoholic diluent; wherein said polymeric resin has a glass transition temperature of about −18° to +80° C., and can bind the water swellable, soluble or sensitive fibers into a nonwoven material without causing the fibers to react to the binder composition.

2. The composition of claim 1 wherein the alkyl acrylate comprises n-butyl acrylate, the alkyl methacrylate comprises methyl methacrylate, and the carboxylic acid comprises acrylic acid, methacrylic acid, or mixtures thereof.

3. The composition of claim 1 wherein said alkali metal hydroxide comprises sodium or potassium hydroxide.

4. The composition of claim 1 wherein said alcoholic diluent comprises methanol, isopropanol, or mixtures thereof.

* * * * *